United States Patent [19]

Tsuk

[11] 3,972,999

[45] Aug. 3, 1976

[54] GRISEOFULVIN DOSAGE FORMS

[75] Inventor: Andrew G. Tsuk, Plattsburg, N.Y.

[73] Assignee: American Home Products Corporation (Del.), New York, N.Y.

[22] Filed: June 25, 1975

[21] Appl. No.: 590,345

[52] U.S. Cl. .................................. 424/78; 424/285
[51] Int. Cl.$^2$ .................. A61K 31/74; A61K 31/34
[58] Field of Search .............................. 424/285, 78

[56] References Cited
OTHER PUBLICATIONS

Florestano – Chem. Abst., vol. 70 (1969), p. 118078e.
Chem. Abst., 8th Coll. Index, vol. 66–75, (1967–1971), p. 14091s.

*Primary Examiner*—Sam Rosen
*Attorney, Agent, or Firm*—Stephen Venetianer

[57] ABSTRACT

Completely miscible melt mixes of amorphous griseofulvin and certain polyglycolides or lactic acid modified polyglycolides are described which are formed by melting together griseofulvin and the polyglycolide or lactic acid modified polyglycolide, the latter having a molecular weight less than 2000 and a glycolic acid content of about 60 to 100 mole per cent. The cooled melt is transparent, glassy and capable of being finely divided. The griseofulvin contained therein, between 30 and 60% by weight, is amorphous and the finely divided melt mixture can be subdivided and incorporated into dosage forms.

4 Claims, No Drawings

GRISEOFULVIN DOSAGE FORMS

DESCRIPTION OF THE INVENTION

This invention relates to completely miscible melt mixes of amorphous griseofulvin and certain polyglycolides or lactic acid modified polyglycolides having systemic absorption rates equivalent to micronized crystalline griseofulvin. The lactic acid modified polyglycolides useful in the invention are those having a molecular weight below about 2000 and a glycolic acid content of about 60 to 100 mole per cent, as described in U.S. Pat. No. 2,362,511 issued Nov. 14, 1944 to Teeters, the disclosure of which is incorporated herein by reference.

The griseofulvin content of the melt mix can range from about 30 to 60% by weight. The melt mixes are formed by simply heating together crystalline griseofulvin and the polyglycollide to a temperature of about 230° to 240°C until the materials melt and form a clear fluid liquid. The liquid is then rapidly cooled and the solid melt can then be subdivided in any conventional manner, as in a mill, and incorporated into dosage forms such as tablets, capsules and the like.

DESCRIPTION OF THE PRIOR ART

Griseofulvin is a water-insoluble and neutral antibiotic usually administered in a micronized crystalline form as described in U.S. Pat. No. 3,330,727. Crystalline griseofulvin has relatively low systemic absorption rates and must be micronized to present a large surface area for more ready dissolution.

In order to increase the dissolution rate of griseofulvin, it has been incorporated into melt mixes with polyethylene glycol (PEG 6000) where in the solidified melt the griseofulvin is in amorphous form. Chiou and Riegelman, *Journal of Pharmaceutical Sciences*, Vol. 58, No. 12, pages 1505–1510; Vol. 59, No. 7, pages 937–942; and Vol. 60, No. 9, pages 1377–1380. In these melts, however, the griseofulvin can be incorporated only up to about 20% by weight since upon subdivision of the melt, the griseofulvin reverts to the crystalline form.

DETAILED DESCRIPTION OF THE INVENTION

The preparation of the glassy melt mixes useful in this invention is described in the following examples.

EXAMPLE 1

The glycolic acid solution was prepared from technical grade glycolic acid by repeated crystallizations and dissolution in distilled water. The final solution contained, by acidimetry, 816 grams per liter of pure glycolic acid. 546 milliliters (about 6 moles) of the glycolic acid solution and 300 milliliters of distilled water were introduced into a 1 liter resin kettle equipped with a nitrogen inlet bubbling tube, thermometer, heating mantle, condenser and receiver. Under a slow stream of nitrogen, water was distilled off under atmospheric pressure until the pot temperature surpassed 140°C. About 340 milliliters of condensate were collected at this point, which was discarded. The distillation was then continued under aspirator vacuum, with nitrogen bubbling through at a reduced rate to provide stirring and to avoid bumping. When the pot temperature reached 200° the distillation was terminated. About 240 milliliters of condensate were collected under vacuum, and also discarded. The resin kettle was opened and its hot contents were poured into a beaker, where it soon solidified to a white opaque brittle mass. It is insoluble in most common solvents and melts around 230°C.

Determination of molecular weight: an amount of the product was dissolved in hot dimethylsulfoxide, and the free carboxyl groups were assayed by non-aqueous acidimetry. The acid number obtained was 1.25 miliequivalents carboxyl per gram of product, corresponding to a number average molecular weight of about 800.

Ten grams of crystalline griseofulvin and 10 grams of the polyglycolide were introduced into a test tube of about 50 ml. volume. The tube was then closed off with a stopper open to the atmosphere through a long narrow glass tube. While held by this tube, the test tube was lowered into an oil bath maintained at a temperature of 230° to 240°C and held there with gentle twirling until the entire contents melted. The melts of the two materials were completely miscible and formed a clear fluid liquid of reddish color. The tube was then held nearly horizontally and rotated slowly under a cold water tap. The fluid melt soon hardened then cracked throughout its mass without losing its transparency. After storage in a freezer, the glassy mix cracked further and was removed from the test tube in the form of chunks. The chunks, remained transparent and brittle even at room temperature.

The chunks were ground in a small laboratory micromill with about 10–15 percent colloidal silica (Cabosil) added as a grinding aid.

The ground sample was kept under normal atmospheric conditions in a glass bottle. Periodic X-Ray assays during the following 33 days revealed no crystallinity.

X-Ray diffraction spectra further showed that as long as the chunks were transparent, the griseofulvin was completely non-crystalline, while a surface haze or whitening signaled some crystallization of griseofulvin.

Another glassy mix prepared in exactly the same way was formulated into capsule dosage forms. The chunks were ground in a micromill after the addition of 15% by weight of Cabosil Grinding aid. The ground powder was sifted through a 100 mesh screen, where most of it passed through. A 50/50 (w/w) mixture of starch and edible lactose was likewise screened, and a 50/50 (w/w) mixture of the latter and the glassy melt was prepared. After thorough mixing, the product was weighed into hard gelatin capsules, hand filled with about 450 mg. each. The final potency was found to average 133 mg griseofulvin per capsule. Twenty seven days after preparation of the capsules, one was assayed by X-Ray diffraction, and was found non-crystalline.

Such capsules were used for in vitro dissolution tests, and for bioabsorption tests perorally in dogs, in comparison with commercial capsules based on microsize crystalline griseofulvin.

Griseofulvin is rapidly and extensively metabolized in vivo to several products but primarily to 6-demethylgriseofulvin (6-DMG) which in turn is partially conjugated with glucoronic acid to glucosiduronic ester. In the tests with dogs, total urinary excretion was analyzed for 6-DMG, the urine being first hydrolyzed enzymatically to convert all conjugated 6-DMG to free 6-DMG.

Four female beagle dogs were used in the tests. Dogs 1 and 2 were given four 125mg. tablets of a commerical brand of micronized griseofulvin (veterinary) and dogs 3 and 4 were given four of the capsules of this example containing on the average 133-mg. of griseofulvin.

The last meal of the dogs was given 16–20 hours pre-medication but water was given ad libitum. The dogs were fed 8 hours after medication. Urine samples were collected at −24 to 0 (pre-medication) and in blocks of 0–24; 24–48 and 48–96 hours.

After seven days, the experiment was repeated with dogs 1 and 2 given the capsules of this example and dogs 3 and 4 given the commercial griseofulvin.

The urine samples were adjusted to pH of 7 and analyzed for 6-DMG, free and total. The total 6-DMG excreted was 68 ± 50 milligrams for the capsules of this example and 64 ± 48 milligrams for the commercial veterinary product.

EXAMPLE 2

Pure crystalline glycollic acid, 351 grams, USP lactic acid (85 percent), 131 milliliters, and 774 milliliters of distilled water were introduced into the resin kettle as in Example 1, and water was distilled off under atmospheric pressure until the pot temperature reached about 180°C and the distillation was then continued under aspirator vacuum until the pot temperature reached 219°C, a total distillation time of about 12 hours. The acid number of the cooled solid melt was 0.543 milliequivalents carboxyl per gram of product, indicating a molecular weight of 1800.

This lactic acid modified polyglycolide containing 75 mole % glycolic acid, with a molecular weight of 1800, was used to make several glassy mixes with griseofulvin as in Example 1. One of these mixes contained 53% by weight griseofulvin, and was kept in the form of chunks for 10 months in a glass bottle. Aside from a white (crystallized) layer on the surfaces, estimated as only 0.04 mm thick, the chunks were transparent, apparently unchanged. Another mix, containing 60% by weight griseofulvin, was kept for 6 months in the form of chunks, then ground for X-Ray diffraction assay. This assay revealed no crystallinity. Upon a further 2 week storage of the ground sample, X-Ray assay showed the presence of a very slight amount of crystallinity.

EXAMPLE 3

Pure crystalline glycolic acid, 217 grams, USP lactic acid (85%), 105 milliliters, and 394 milliliters of distilled water were introduced into the resin kettle as in Example 1, and water was distilled off under atmospheric pressure until the pot temperature reached about 180°C and the distillation was then continued under aspartic vacuum until the pot temperature reached 205°C, a total distillation time of about 10 hours. The acid number of the cooled solid melt was 0.819 milliequivalents carboxyl per gram of product, indicating a molecular weight of 1200.

Two parts by weight of this lactic acid modified polyglycolide containing 70 mole % glycolic acid, with a molecular weight of 1200, and one part of griseofulvin were made into a glassy mix as in Example 1. It was ground in a micromill, and an assay 3 days later revealed it as non-crystalline.

EXAMPLE 4

Glycolic acid in aqueous solution, 570 milliliters containing 465 grams of acid, USP lactic acid (85%), 140 milliliters, and 470 milliliters of distilled water were introduced into the resin kettle as in Example 1, and water was distilled off under atmospheric pressure until the pot temperature reached about 180°C and the distillation was then continued under aspirator conditions until the pot temperature reached 255°C, a total distillation time of about 16 hours. The acid number of the cooled solid melt was 0.670 milliequivalents carboxyl per gram of product, indicating a molecular weight of 1500.

One part by weight of this lactic acid modified polyglycolide containing 79 mole % glycolic acid, with a molecular weight of 1500, and one part of griseofulvin were made into a glassy mix as in Example 1. It was ground and kept for 4 days under normal atmospheric conditions after which it assayed as non-crystalline. Another ground sample was kept at 100 percent relative humidity for a day, after which it assayed as completely crystalline. This indicates that crystallization is promoted by moisture, and that moisture exposure is the likely reason for the surface crystallinity described in Example 1.

EXAMPLE 5

Glycolic acid in aqueous solution, 314 milliliters containing 794 milligrams per milliliter by titration, USP lactic acid (85 percent), 190 milliliters, and 300 milliliters of distilled water were introduced into the resin kettle as in Example 1 and water was distilled off under atmospheric pressure until the pot temperature reached about 180°C and the distillation was then continued under aspirator conditions until the pot temperature reached 201°C, a total of about 16 hours. The acid number of the cooled solid melt was 0.81 milliequivalents carboxyl per gram of product, indicating a molecular weight of 1200.

One part by weight of this lactic acid modified polyglycolide containing 63 mole % of glycolic acid and one part by weight of griseofulvin were made into a glassy mix as in Example 1.

Polyester resins containing 60 mole % to 100 mole % glycolic acid (the remainder being lactic acid) prepared according to this invention are effective in maintaining high levels of griseofulvin (30 to 60 percent) in amorphous form even when ground and stored.

As the glycolic acid content increases, the resulting glassy mixes become harder, their softening point increases, and they show less tendency towards caking, all of these being desirable changes. Also, the color of the mix deepens from amber to red. Polyester resins with a glycolic acid content below about 80 mole % are transparent brittle solids melting at or below 60°C. Preferably, therefore, the melts having a glycolic acid content above 80 mole %, i.e. from about 80 to 100 mole %, are employed to form the griseofulvin containing glass melts of this invention.

As can be appreciated by one skilled in the art, an alternative to the method of mixing employed in the examples is to add the crystalline griseofulvin to the molten polyglycolide or lactic acid modified glycolide at the end of the distillation.

I claim:

1. A solid glassy miscible melt mix comprising about 30 to 60% by weight of the mix of amorphous griseofulvin and a polyglycolide or lactic acid modified polyglycolide, the polyglycolide having a molecular weight of about 800 to about 2000 and a glycolic acid content of about 60 to 100 mole per cent.

2. The solid glassy melt mix of claim 1 wherein the polyglycolide has a molecular weight of about 800 to about 1500 and a glycolic acid content of about 80 to 100 mole per cent.

3. A griseofulvin dosage form comprising an encapsulated finely divided glassy melt mix of claim 2.

4. A process for preparing a solid glassy melt mix containing amorphous griseofulvin which comprises, a. reacting at a temperature of 180° to 200°C. glycolic acid in the presence of water with about 0 to 40 mole per cent, based on the glycolic acid, of lactic acid until substantially all of the water has been removed to form a polyglycolide, and b. admixing with the polyglycolide crystalline griseofulvin at a temperature of about 230° to 240°C in an amount sufficient to provide about 30 to 60% by weight of the glassy melt mix.

* * * * *